United States Patent [19]
Fricke et al.

[11] Patent Number: 5,396,015
[45] Date of Patent: Mar. 7, 1995

[54] PROCESS FOR SKELETAL ISOMERIZATION OF N-ALKENES

[75] Inventors: Rolf Fricke; Gerhard Ohlmann; Udo Roost; Heide L. Zubowa, all of Berlin; Dieter Timm, Halle; Karl Becker, Bad Kosen; Helmut Striegler, Halle, all of Germany

[73] Assignee: Veba Oel AG, Gelsenkirchen, Germany

[21] Appl. No.: 983,059

[22] Filed: Nov. 30, 1992

[30] Foreign Application Priority Data

Nov. 30, 1991 [DE] Germany .................. 41 39 552.2

[51] Int. Cl.⁶ .................................................. C07C 5/27
[52] U.S. Cl. ................................................... 585/671
[58] Field of Search .......................................... 585/671

[56] References Cited

U.S. PATENT DOCUMENTS 5,107,050  4/1992  Gaffney et al. ................ 585/671

FOREIGN PATENT DOCUMENTS

| | | |
|---|---|---|
| 0103117 | 3/1984 | European Pat. Off. . |
| 0131946 | 1/1985 | European Pat. Off. . |
| 0132708 | 2/1985 | European Pat. Off. . |
| 0158348 | 10/1985 | European Pat. Off. . |
| 0158975 | 10/1985 | European Pat. Off. . |
| 0161489 | 11/1985 | European Pat. Off. . |
| 0161490 | 11/1985 | European Pat. Off. . |
| 0161491 | 11/1985 | European Pat. Off. . |

*Primary Examiner*—Helen M. S. Sneed
*Assistant Examiner*—E. D. Irzinski
*Attorney, Agent, or Firm*—Antonelli, Terry, Stout & Kraus

[57] ABSTRACT

Skeletal isomerization of n-alkenes into isoalkenes and enrichment of isoalkenes in alkene-containing hydrocarbon mixtures is effected in the presence of an isomerization catalyst containing a microporous silicon-containing alumophosphate.

A goal of the method for skeletal isomerization is to provide a running time in one operating period of over 100 hours. This goal is achieved by using, as isomerization catalysts, microporous alumophosphates with a molecular sieve structure whose pore inlet openings have a diameter of 0.4 to 0.6 nm which are mixed with a binder and activated at temperatures of 623 to 873K.

6 Claims, 1 Drawing Sheet

IR SPECTRUM OF ACTIVATED SiO₂

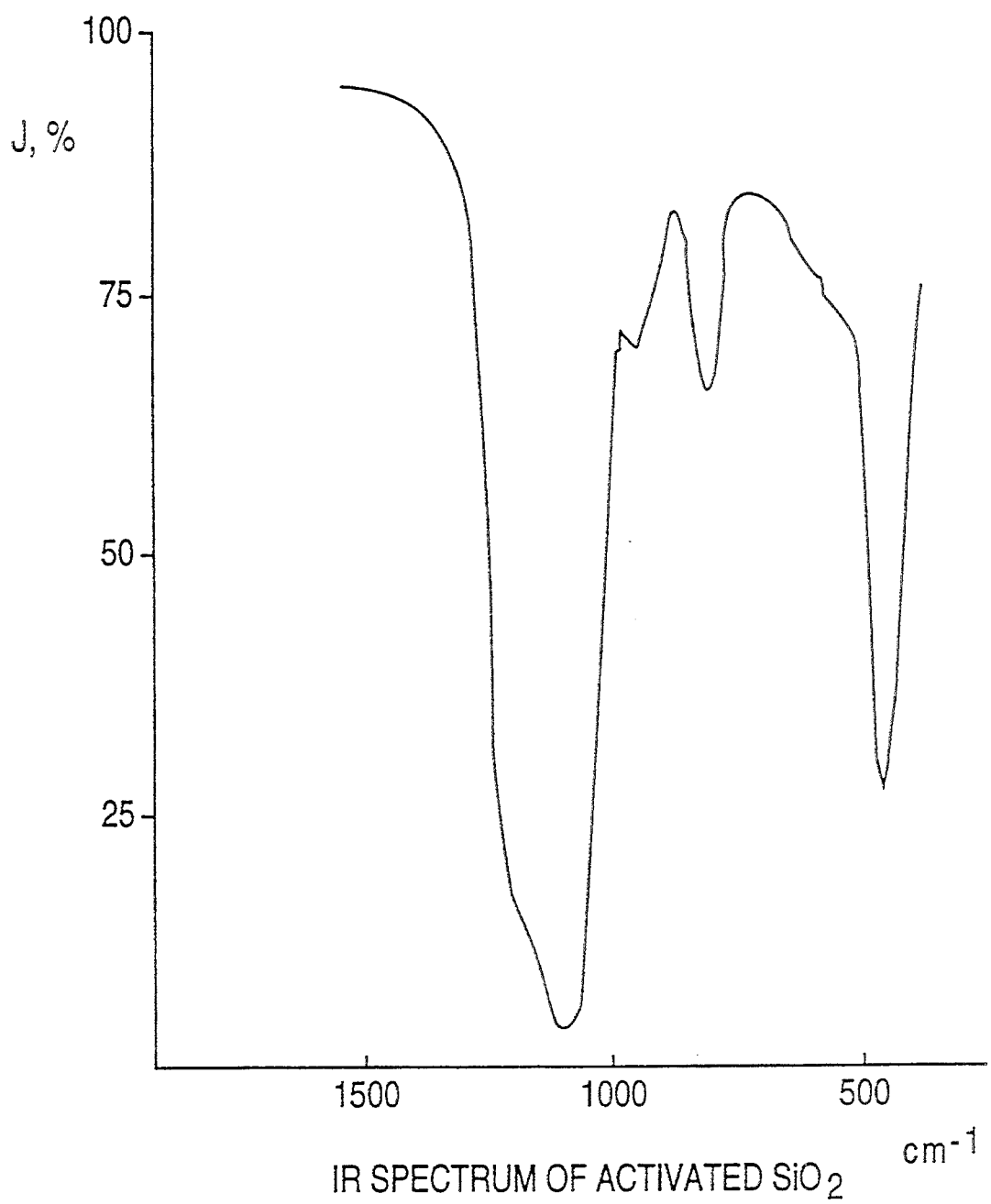
IR SPECTRUM OF ACTIVATED SiO₂

PROCESS FOR SKELETAL ISOMERIZATION OF N-ALKENES

The invention relates to a process for skeletal isomerization of n-alkenes into isoalkenes, and for enrichment of isoalkenes in n-alkene-containing hydrocarbon mixtures.

Catalytic isomerization of n-alkenes into isoalkenes is already known. In this method, both halogen-containing and halogen-free catalysts are used for isomerization. With halogen-containing catalysts, in some cases catalyst operating times of 100 hours are reached (DE 3040698, DE 3137383). However, these catalysts have the disadvantage that their halogen component is continuously carried away with the isomerization product, particularly if it contains water, causing it continuously to lose effectiveness. Therefore, for retention of catalytic activity, it is necessary to continue adding fresh halogen to the catalyst. A further disadvantage of using such catalysts is that the apparatus must be made of halogen-resistant materials.

Using oxidic catalysts based on aluminum oxide, silicon dioxide, possibly with addition of further oxides (U.S. 2,216,285, SU 551315) of metals or their compounds (DE 2059619, EP 66485) or surface-treated with silicon organic compounds (DE 3340958, ES 440497, U.S. 4,038,337, SU 137727) in a halogen-free process is also known.

The use of phosphate-containing (DE 971849, U.S. 2,281,804, U.S. Pat. No. 2,554,202, U.S. Pat. No. 3,448,104, GB 602202, GB 635508) or phosphoric acid-containing (U.S. Pat. No. 2,220,693, FR 823545) or sulfate-containing (F.K. Serebryakova, Compt. rend. acad. sci. (USSR) IV, 359 (1936); J.C. Luy, Reakt. Kin. Cat. Lett., Vol. 36, No. 2, 273–279 (1988) catalysts is also known. However, all these catalysts have the disadvantage that the best attainable catalysis times are less than 70 hours and/or there is considerable byproduct formation.

The goal of the invention is to avoid the above-stated disadvantages of known processes. Thus, the task is to develop a process of skeletal isomerization of n-alkenes into isoalkenes and enrichment of isoalkenes in alkene-containing hydrocarbon mixtures in which catalysis times of over 100 hours can be achieved in one operating period avoiding the use of halogen-containing catalysts. This problem is solved according to the invention by a process of skeletal isomerization of n-alkenes into isoalkenes and enrichment of isoalkenes in alkene-containing hydrocarbon mixtures at temperatures of 593 to 823K and pressures of 98 to 2100 kPa, possibly in the presence of inert gases and/or hydrogen, by using, as the isomerization catalyst, a microporous alumophosphate with a molecular sieve structure and pore inlet openings of 0.4 to 0.6 nm, which is mixed with a binder and shaped in known fashion then activated at temperatures of 623 to 873K.

It has proven advantageous for skeletal isomerization of n-alkenes into isoalkenes to use alumophosphates which have silicon and/or bivalent metals in the skeleton and/or lattice and characterized in the x-ray diffraction diagram (Cu-K-alpha radiation) by interferences in at least the following lattice plane ranges: d(A): 2.8 to 3.0; 3.8 to 4.1; 4.0 to 4.5; 10 to 12.

Such alumophosphates crystallize from gel-like reaction mixtures which consist of an aluminum compound, a phosphorus compound, a silicon compound, water, possibly a compound of bivalent metals, and a structure-directing compound, at temperatures between 423 and 473K under autogenous pressure in steel autoclaves lined for example with Teflon R. The structure-directing compounds that may be used are secondary amines or quaternary ammonium compounds. Particularly suitable as a silicon source is activated $SiO_2$, made for example by a preliminary grinding process, that possesses predominantly spherical particles with a diameter of approximately 2 nm and has the IR spectrum shown in FIG. 1.

Orthophosphoric acid is advantageously used as the phosphorus compound and aluminum oxide hydrate compounds, primarily pseudoboehmite or aluminum hydroxide, are used as the aluminum source. Sulfates, acetates, and chlorides of zinc, manganese, magnesium, iron, cobalt, and mixtures thereof are used predominantly as metal compounds. Also combinations with hydrogenation-active components in amounts of 0.01 to 2 wt. %, based on the catalyst, particularly palladium, are suitable. Suitable molar ratios for the reaction mixture are:

$SiO_2/Al_2O_3$—0.08 to 0.5
$P_2O_5/Al_2O_3$—0.8 to 1.2
$H_2O/Al_2O_3$—30.0 to 60.0
$MeO/Al_2O_3$—0.004 to 0.025.

The molar ratio between the structure-directing compound and the $Al_2O_3$ portion is in the range of 0.8 to 1.2. The activated catalyst component is shaped in known fashion after mixing with a binder by, for example, extrusion, dripping, agglomeration, or molding, then activated at 623 to 873K. Pseudoboehmite, silicic acid, or laminar silicates, particularly magadiite, are suitable as binders. These catalysts are outstandingly suitable for skeletal isomerization of n-alkenes into isoalkenes and for enriching isoalkenes in n-alkene-containing hydrocarbon mixtures.

For skeletal isomerization, linear isomerizable olefins, either pure or mixed with other hydrocarbons, particularly alkanes, dried or water-containing, for example water-saturated, are used. The olefin-containing mixtures can come for example from processing pyrolysis products or be residual gas mixtures from syntheses, for example from synthesis of methyl tert-butyl ether. They can contain multiply unsaturated compounds or be hydrated to remove them. Olefin isomerization can be carried out with addition of up to 95 vol. % inert substances such as nitrogen, carbon dioxide, or hydrogen or gases containing these or water. In the extensive conversion of n-olefins to isoolefins, which is the goal, a production cycle is useful.

The catalyst loading is 1 to 30 g/g catalyst. hour, preferably 2 to 10 g/g catalyst,hour, based on the olefin. The reaction temperature is 593 to 823K. If the input substance has a high 1-olefin content, for example a high butene-1 content, isomerization can be conducted in two stages and at temperatures below 573K first a double bond isomerization is effected, e.g. from butene-1 to butene-2, then the product so obtained is isomerized at temperatures over 573K to the skeleton, for example to isobutene. Of course the mixture obtained from stage 1, butene-2-rich for example, can also be used for other syntheses, for example for alkalization of aromatic hydrocarbons.

The reaction pressure is not critical. For isomerization, it is advantageous to adjust the connected apparatus to the system pressure, for example the system supplying the starting mixture or the one used for preparation. It is preferable operate in the pressure range between 98 and 2100 kPa. The composition of the reaction products is determined by gas chromatography with silver-nitrate-saturated benzyl cyanide on porolith. With the catalysts described, which can be used in solid and fluidized beds, a high selectivity of isoolefin is achieved under the aforementioned reaction conditions, whereby the reaction product contains less than 3 or 2% of cracking or high-boiling components. The catalyst running time in one operating period is over 300 hours under favorable reaction conditions. When the catalyst activity tapers off, its efficiency can be restored in the usual manner by burning the precipitated carbon with oxygen or oxygen-containing gases, possibly with addition of steam, at 673 to 973K.

EXAMPLE 1

A homogenous suspension is produced from 8.48 g pseudoboehmite (75.0 wt. % $Al_2O_3$), 11.5 g orthophosphoric acid (85.0 wt. %, p.a.), and 21.3 g distilled water at a temperature of 293±2K with stirring for 1 hour. After dilution with 30.4 g water, 5.1 g di-n-propylamine (99.0 wt. %, Merck) is added with further stirring. The gel with the composition 0.8 di-n-propylamine: 1.0 $Al_2O_3$: 0.8 $P_2O_5$: 49.5 $H_2O$ molar parts is aged at 298±2K and crystallized in a Teflon container in a steel autoclave (volume 90 ml) at 473±2K over a period of 24 hours. The crystallization product is separated from the mother liquor, washed neutral with distilled water, and dried at 303K. To remove the structure-directing compound, the sample is baked for 7 hours at 873±2K in air. 2.0 g of template-free substance is mixed with 1.08 g Aerosil 200 (Degussa) and 5.0 g water into a paste and, using an extrusion press, processed into strands 1 mm in diameter with an average length of 3 mm which are dried at 393K. The template-free sample has the x-ray reflexes listed in the table.
Pore diameter: 0.53 nm

TABLE

| X-ray Reflexes | | |
| --- | --- | --- |
| d | | Intensity |
| 10.28 | 10.65 | very strong |
| 4.31 | 4.40 | weak to strong |
| 4.0 | 4.21 | weak to strong |
| 3.80 | 3.99 | very strong |
| 2.80 | 2.82 | weak |

EXAMPLE 2

8.14 g pseudoboehmite, 21.3 g water, and 1.75 g activated silicon dioxide (see FIG. 1 for IR spectrum) are mixed and stirred for two hours. 11.5 g concentrated orthophosphoric acid is added to the mixture, which is further stirred. Once the desired homogeneity has been reached, the suspension is diluted with 11.0 g water and reacted with 5.1 g di-n-propylamine. The reaction gel has the following composition: 0.8 di-n-propylamine: 1.0 $Al_2O_3$: 0.8 $P_2O_5$: 0.5 $SiO_2$: 33.4 $H_2O$ (molar parts). Hydrothermal treatment and following processing of the crystallizate are conducted according to Example 1. The x-rays of the samples show the reflexes given in the table.

From 4.0 g active component, 2.84 g pseudoboehmite, 0.12 ml nitric acid (65.0 wt. %, p.a.), 0.40 g starch paste (9.0 wt. % starch), and 3.7 g water, a paste was made which was molded into strands as in Example 1. The strands were tempered in steps for 1 hour at 413K, 1 hour at 513K, and 3 hours at 873K.
Pore diameter: 0.55 nm

EXAMPLE 3

A mixture of 5.0 g pseudoboehmite and 7.0 g active component, made according to Example 1, was peptized with 10.22 g nitric acid (50.0 wt. %) and 4.12 g water, and dripped in an ammonia column (8.0 wt.% $NH_4OH$) to form spheres.
Pore diameter: 0.53 nm

EXAMPLE 4

For synthesis of a manganese silicoalumophosphate molecular sieve, 8.14 g pseudoboehmite, 0.34 g $MnSO_4 \cdot 4 H_2O$ (p.a.), 0.29 g of $SiO_2$ activated by grinding, and 31.0 g water were assembled and stirred for 1 hour at room temperature. Shortly before the end of the stirring time, 11.3 g of orthophosphoric acid (85 wt. %) was added. The material was stirred for another hour. It was then diluted with 30.0 g water and 7.26 g di-n-propylamine was added. Half an hour of intensive stirring was necessary because sudden suspension thickening occurred. The gel with the composition 1.2 di-n-propylamine: 1.0 $Al_2O_3$: 0.82 $P_2O_5$: 0.025 MnO: 0.08 $SiO_2$: 60 $H_2O$ (molar parts) was crystallized under the conditions listed in Example 1. The crystallization product was then treated as in Example 1. The product had the x-ray reflexes listed in the table. The amine-free substance was made into strands with Aerosil 200 according to Example 1.
Pore diameter: 0.54 nm

EXAMPLE 5

A zinc silicoalumophosphate molecular sieve was made according to Example 4. When the gel was prepared, 0.07 g $ZnSO_4 \cdot 7 H_2O$ (p.a.) was accordingly used. The gel composition was 1.2 di-n-propylamine: 1.0 $Al_2O_3$: 0.82 $P_2O_5$: 0.004 ZnO: 0.8 $SiO_2$: 60 $H_2O$ (molar parts).
Pore diameter: 0.54 nm

EXAMPLE 6

0.29 g activated silicon dioxide, 0.35 g $FeSO_4 \cdot 7 H_2O$ (p.a.), 16.59 g orthophosphoric acid, and 30.5 g water were mixed in an Erlenmeyer flask 1 for 15 minutes with a magnetic stirrer. In parallel, 8.14 g pseudoboehmite, 30.0 g water, and 7.26 g di-n-propylamine were stirred in a second flask for 15, minutes. The contents of flask 1 were added to flask 2. Stirring continued for a further 30 minutes. The gel with the composition 1.2 di-n-propylamine: 1.0 $Al_2O_3$: 1.2 $P_2O_5$: 0.08 $SiO_2$: 0.02 FeO: 60 $H_2O$ (molar parts) was then processed as in Example 1.
Pore diameter: 0.55 nm

EXAMPLE 7

A magnesium silicoalumophosphate molecular sieve was produced similarly to Example 6. In gel preparation, 0.31 g $MgSO_4 \cdot 7 H_2O$ was accordingly used. The gel composition was 1.2 di-n-propylamine: 1.0 $Al_2O_3$: 1.2 $P_2O_5$: 0.08 $SiO_2$: 0.02 MgO: 60 $H_2O$ (molar parts).
Pore diameter: 0.55 nm

EXAMPLE 8

50 ml of a catalyst according to Example 4 was placed in a reactor 430 mm long with a diameter of 25 mm. The catalyst was loaded at 743 K and a total pressure of 102 kPa with 3 g/g catalyst/hour of a residual hydrocarbon mixture from the synthesis of methyl tert-butyl ether with the following composition (in wt.%):

| | |
|---|---|
| Propane | 0.05 |
| Propene | 0.12 |
| Isobutane | 4.24 |
| n-Butane | 17.40 |
| Isobutene | 0.18 |
| Butene-1 | 48.62 |
| Trans-butene-2 | 12.21 |
| Cis-butene-2 | 17.10 |

After 315 hours' loading time, 42.1% conversion of the n-butenes, isobutene selectivity of 93.3%, and an isobutene yield of 39.3% were obtained. After 320 hours, addition of the hydrocarbon mixture was ended and the catalyst was heated to 773K under a nitrogen stream of 5 l/h. Once this temperature was reached, it was treated for 6 hours with air to regenerate the catalyst. The reactor temperature was then lowered to 743K under a nitrogen stream of 5 l/h. Once this temperature was reached, the nitrogen stream was turned off and the catalyst was then treated once more with the hydrocarbon mixture under the same conditions. After a further four regenerations, 38.4% n-butene conversion, 87.1% isobutene selectivity, and 33.4% isobutene yield were obtained after 2016 hours.

EXAMPLE 9

50 ml of a catalyst according to Example 1 was placed in a reactor according to Example 8. The catalyst was loaded at 723K and a total pressure of 1430 kPa with 6 g/g catalyst/hour of a residual hydrocarbon mixture from the synthesis of methyl tert-butyl ether with the composition in Example 8 with additional feed of 15 l/h hydrogen. After 310 hours, n-butene conversion of 33%, isobutene selectivity of 91.2%, and isobutene yield of 30.1% were obtained.

EXAMPLE 10

50 ml of a catalyst according to Example 3 was placed in a reactor according to Example 8. The catalyst was loaded at 623 K and a total pressure of 102 kPa with 1 g/g catalyst-hour of a residual hydrocarbon mixture from synthesis of methyl tert-butyl ether with the composition shown in Example 8 with further addition of 30 l/h nitrogen. After 305 hours, an n-butene conversion of 34.3%, isobutene selectivity of 79.7%, and isobutene yield of 27.3% were obtained.

EXAMPLE 11

50 ml of a catalyst according to Example 2 was placed in a reactor according to Example 8. The catalyst was loaded at 773K and a total pressure of 102 kPa with 2 g/g catalyst-hour of a residual hydrocarbon mixture from synthesis of methyl tert-butyl ether with the composition in Example 8 with further addition of 25 g/h water. After 280 hours, an n-butene conversion of 39.5%, isobutene selectivity of 83.2%, and isobutene yield of 32.9% were obtained.

EXAMPLE 12

50 ml of a catalyst according to Example 4 was placed in a reactor according to Example 8. The catalyst was loaded at 823K and a total pressure of 2040 kPa with 9 g/g catalyst-hour of a residual hydrocarbon mixture with the following composition (in wt.%):

| | |
|---|---|
| Propane | 0.09 |
| Propene | 0.19 |
| Isobutane | 7.16 |
| n-Butane | 18.76 |
| Isobutene | 0.25 |
| Butene-1 | 57.93 |
| Trans-butene-2 | 18.29 |
| Cis-butene-2 | 23.22 |
| $C_{5+}$ hydrocarbons | 0.11 |

After 260 hours, an n-butene conversion of 35.7%, isobutene selectivity of 88.6%, and isobutene yield of 31.6% were obtained.

EXAMPLE 13

50 ml of a catalyst according to Example 1 was placed in a reactor according to Example 8. The catalyst was loaded at 753K and a total pressure of 1430 kPa with 20 g/g catalyst-hour of a residual hydrocarbon mixture from synthesis of methyl tert-butyl ether with the following composition (in wt.%):

| | |
|---|---|
| Propane | 1.09 |
| Propene | 0.74 |
| Isobutane | 12.81 |
| n-Butane | 8.25 |
| Isobutene | 0.28 |
| Butene-1 | 59.90 |
| Trans-butene-2 | 7.12 |
| Cis-butene-2 | 9.40 |
| $C_{5+}$ hydrocarbons | 0.36 |
| Butadiene | 0.05 |

After 170 hours, n-butene conversion of 26.5%, isobutene selectivity of 89.4%, and isobutene yield of 23.7% were obtained.

EXAMPLE 14

50 ml of a catalyst according to Example 4 was placed in a reactor according to Example 8. The catalyst was loaded at 673K and a total pressure of 102 kPa with 2 g/g catalyst-hour of a residual hydrocarbon mixture from synthesis of methyl tert-butyl ether with the composition in Example 13 with further addition of 20 l/h hydrogen. After 275 hours, an n-butene conversion of 37.2%, isobutene selectivity of 91.1%, and isobutene yield of 33.9% were obtained.

EXAMPLE 15

50 ml of a catalyst according to Example 4 was placed in a reactor according to Example 8. The catalyst was loaded at 733K and a total pressure of 102 kPa with 3 g/g catalyst-hour of a butene mixture of 98.2% butene-1, 0.7% trans-butene-2, and 1.1% cis-butene-2. After 328 hours, an n-butene conversion of 41.6%, isobutene selectivity of 92.2%, and isobutene yield of 38.4% were obtained.

EXAMPLE 16

50 ml of a catalyst according to Example 6 was placed in a reactor according to Example 8. The catalyst was loaded at 713K and a total pressure of 150 kPa with 7 g/g catalyst-hour of a butene mixture according to Example 15 with further addition of 10 l/h hydrogen. After 310 hours, an n-butene conversion of 36.9%, isobutene yield of 31.9%, and isobutene selectivity of 86.4%, were obtained.

EXAMPLE 17

50 ml of a catalyst according to Example 5 was placed in a reactor according to Example 8. The catalyst was loaded at 703K and a total pressure of 150 kPa with 2 g/g catalyst·hour of a butene mixture according to Example 15 with further addition of 50 g/h water. After 160 hours, an n-butene conversion of 35.2%, isobutene selectivity of 91.2%, and isobutene yield of 32.1% were obtained.

EXAMPLE 18

50 ml of a catalyst according to Example 2 was placed in a reactor according to Example 8 to which 0.01 wt. % palladium had been added by impregnation with palladium nitrate. The catalyst was loaded at 733K and a total pressure of 102 kPa with 3 g/g catalyst hour of a residual hydrocarbon mixture from synthesis of methyl tert-butyl ether with the composition given in Example 8 with further addition of 30 l/h hydrogen. After 360 hours, an n-butene conversion of 39.8%, isobutene selectivity of 92.0%, and isobutene yield of 36.6% were obtained.

EXAMPLE 19

50 ml of a catalyst according to Example 4 was placed in a reactor according to Example 8. The catalyst was loaded at 503K and a total pressure of 150 kPa with 3 g/g catalyst·hour of a butene mixture of 98.2% butene-1, 0.7% trans-butene-2, and 1.1% cis-butene-2. After 240 hours, an n-butene-1 conversion of 78.3%, cis-butene-2 selectivity of 37.5%, and trans-butene-2 selectivity of 62.5% were obtained. The entire reaction product was conducted over 50 ml of the same catalyst into a second reactor with a load of 3 g/g catalyst·hour with the butene mixture at a temperature of 743K and a total pressure of 150 kPa. After 240 hours, an n-butene conversion of 40.1% and an isobutene selectivity of 93.2%, and isobutene yield of 37.4% were obtained.

EXAMPLE 20

50 ml of a catalyst according to Example 7 was placed in a reactor according to Example 8. The catalyst was loaded at 663K and a total pressure of 150 kPa with 3 g/g catalyst·hour with a hydrocarbon mixture having the following composition (in wt.%):

| | |
|---|---|
| $C_3$ hydrocarbons | <0.05 |
| Isobutane | 4.1 |
| n-Butane | 15.3 |
| Isobutene | 42.5 |
| Butene-1 | 22.7 |
| Trans-butene-2 | 8.8 |
| Cis-butene-2 | 6.1 |
| Butadiene | 0.3 |
| $C_{5+}$ hydrocarbons | <0.1 |
| Water | <0.05 |

After 335 hours, an n-butene conversion of 35.6%, isobutene selectivity of 92.3%, and isobutene yield of 32.9% were obtained.

EXAMPLE 21

1.84 g of a catalyst according to Example 4 is placed in an electrically heated steel reactor 10 mm in diameter and 200 mm long and loaded at 743K with 3.6 l/h of a mixture of 14.5 vol. % hexene-1 in nitrogen. The reaction product is frozen out and analyzed by gas chromatography. It had the following composition (in wt.%):

| | |
|---|---|
| 3-methylpent-1-ene | 3.2 |
| 2,3-dimethylbut-1-ene | 5.6 |
| 4-methylpent-2-ene (cis + trans) | 4.6 |
| 2-methylpent-1-ene | 10.0 |
| n-hexene (-1,-2,-3) | 23.0 |
| 2-ethylbut-1-ene | 5.4 |
| 2-methylpent-2-ene | 16.5 |
| 2-methylpent-2-ene (cis) | 9.2 |
| 3-methylpent-2-ene (trans) | 13.8 |
| Methylcyclopentane | 3.2 |
| 3,3-dimethylbut-2-ene | 5.5 |

We claim:

1. A method for skeletal isomerization of n-alkenes into isoalkenes and enrichment of isoalkenes in alkene-containing hydrocarbon mixtures which comprises isomerizing n-alkenes at temperatures of 593 to 823K and pressures of 98 to 2100 kPa in the presence of an isomerization catalyst, the isomerization catalyst comprising a microporous alumophosphate with a molecular sieve structure and with pore inlet openings of 0.4 to 0.6 nm diameter admixed with a binder, shaped, and then activated at temperatures of 623 to 873K; said alumophosphate containing silicon and at least one metal in a lattice structure having an X-ray diffractogram (Cu-K-alpha radiation) characterized by interferences in at least the following lattice plane ranges: d(A) : 2.8 to 3.0; 3.8 to 4.1; 4.0 to 4.5; 10 to 12; and the silicon contained in the alumophosphate comprising silicon of activated silicon dioxide which exhibits an IR spectrum according to FIG. 1 thereby producing isoalkenes.

2. A method according to claim 1, wherein the activated silicon dioxide providing the silicon contained in the alumophosphate comprises spherical particles having a diameter of 2 nm.

3. A method according to claim 1, wherein the at least one metal contained within said alumophosphate is a bivalent metal selected from the group consisting of zinc, manganese, magnesium, iron and cobalt and mixtures thereof.

4. A method according to claim 1, wherein the binder comprises pseudoboehmite, silicic acid or laminar silicates including magadiite.

5. A method according to claim 1, wherein the catalyst further comprises a hydrogenation active component, comprising palladium in an amount of 0.01 to 0.2 weight %.

6. A method according to claim 3, wherein the alumophosphate of the isomerization catalyst comprises a reaction mixture having the following molar ratios of components:
$SiO_2/Al_2O_3$: 0.08 to 0.5;
$P_2O_5/Al_2O_3$: 0.8 to 1.2;
$H_2O/Al_2O_3$: 30.0 to 60.0; and
$MeO/Al_2O_3$: 0.004 to 0.025
wherein Me represents the at least one bivalent metal.

* * * * *